US012508154B2

(12) United States Patent
Peesay et al.

(10) Patent No.: US 12,508,154 B2
(45) Date of Patent: Dec. 30, 2025

(54) PORTABLE FOLDING INFANT RADIANT WARMER

(71) Applicant: Georgetown University, Washington, DC (US)

(72) Inventors: Morarji Peesay, Germantown, MD (US); Prasad Muddam, Washington, DC (US)

(73) Assignee: Georgetown University, Washington, DC (US)

( * ) Notice: Subject to any disclaimer, the term of this patent is extended or adjusted under 35 U.S.C. 154(b) by 814 days.

(21) Appl. No.: 17/623,436

(22) PCT Filed: Jun. 30, 2020

(86) PCT No.: PCT/US2020/040232
§ 371 (c)(1),
(2) Date: Dec. 28, 2021

(87) PCT Pub. No.: WO2021/003121
PCT Pub. Date: Jan. 7, 2021

(65) Prior Publication Data

US 2022/0347008 A1 Nov. 3, 2022

Related U.S. Application Data

(60) Provisional application No. 62/869,295, filed on Jul. 1, 2019.

(51) Int. Cl.

| | |
|---|---|
| ***A61F 7/00*** | (2006.01) |
| ***A61G 11/00*** | (2006.01) |
| ***A61G 13/10*** | (2006.01) |

(52) U.S. Cl.
CPC ............ *A61F 7/0053* (2013.01); *A61G 11/00* (2013.01); *A61G 13/105* (2013.01); (Continued)

(58) Field of Classification Search
CPC ............ A61F 2007/0088; A61G 11/00; A61G 13/105
See application file for complete search history.

(56) References Cited

U.S. PATENT DOCUMENTS 3,470,866 A * 10/1969 Gittelson ............... A61G 11/00 600/22
3,858,570 A 1/1975 Beld et al.
(Continued)

FOREIGN PATENT DOCUMENTS

WO WO-2012006545 A2 * 1/2012 ........... A47C 21/044

OTHER PUBLICATIONS

International Search Report and Written Opinion for PCT International Patent Application No. PCT/US2020/040232, dated Sep. 22, 2020.

*Primary Examiner* — Kaitlyn E Smith
(74) *Attorney, Agent, or Firm* — Klarquist Sparkman, LLP

(57) ABSTRACT

A reconfigurable, foldable, and manually transportable infant radiant warmer. In a collapsed configuration, the warmer consumes a minimal amount of space and can be manually transported easily. In a deployed configuration, the warmer provides open access to an infant lying on a bed platform for receiving resuscitative therapy and warmth from a radiant heater disposed upon an adjacent mast. The reconfigurable infant radiant warmer includes mutually reconfigurable bed, mast, and suspension modules. The mast module and the suspension module may be selectively moved relative to the bed module to achieve the collapsed configuration.

33 Claims, 4 Drawing Sheets

Folding Mode

(52) U.S. Cl.
CPC ................. *A61F 2007/0052* (2013.01); *A61F 2007/0084* (2013.01); *A61F 2007/0088* (2013.01); *A61F 2007/0096* (2013.01)

(56) References Cited

U.S. PATENT DOCUMENTS

| | | | | | |
|---|---|---|---|---|---|
| 3,868,570 | A * | 2/1975 | Kopera, Jr. | G01P 1/07 | 377/55 |
| 4,628,553 | A | 12/1986 | Buttitta et al. | | |
| 5,811,760 | A * | 9/1998 | Siebelink | H05B 3/30 | 219/217 |
| 5,980,449 | A * | 11/1999 | Benson | A47C 21/048 | 600/22 |
| 2001/0049465 | A1 * | 12/2001 | Goldberg | A61M 16/16 | 600/22 |
| 2002/0070532 | A1 * | 6/2002 | Harrison | A61G 5/0825 | 280/647 |
| 2011/0124952 | A1 * | 5/2011 | Panicker | F01K 13/00 | 392/407 |
| 2011/0245583 | A1 * | 10/2011 | Vyasarao | A61N 5/0625 | 600/22 |
| 2013/0312179 | A1 | 11/2013 | Bharadwaj et al. | | |

* cited by examiner

PORTABLE FOLDING INFANT RADIANT WARMER

RELATED APPLICATIONS

This application is a 35 U.S.C. § 371 filing of International Patent Application No. PCT/US2020/040232, filed Jun. 30, 2020, which claims priority to U.S. Provisional Application No. 62/869,295, filed Jul. 1, 2019, the contents of which are incorporated herein in their entirety.

FIELD OF THE DISCLOSURE

The disclosure herein relates generally to the field of infant radiant warming. More particularly, the present disclosure relates to a portable, foldable infant radiant warmer which provides not only thermal stability but also resuscitation resources.

BACKGROUND

Childbirth in communities having less sophisticated healthcare infrastructure has a higher risk of infant mortality that could be remediated through simple but effective interventions. One such intervention involves the use of infant radiant warmers. Infant radiant warmers are frequently used in delivery rooms to receive newborn babies immediately after delivery. The heat loss in some newborns is rapid and without compensation can lead to life-threatening complications. Radiant warmers are used to maintain the body temperature of newborn infants, thus minimizing the energy expended for metabolic heat production. Common examples of radiant warmers may incorporate some form of servo control to facilitate the maintenance of substantially constant body temperature.

Many newborns, both mature term and premature infants, are born outside of delivery rooms, such as at home or in other under-resourced settings, unexpectedly due to maternal reasons or due to unavoidable circumstances. Infants born outside of delivery rooms are vulnerable to uncontrolled environmental temperatures and the absence of routine resuscitative measures, factors which can increase morbidity and mortality, especially in premature infants. In such settings, urgent newborn care, including temperature maintenance and ventilation support, is needed to stabilize the baby prior to transport to a hospital maternity facility for further management. Currently available radiant warmers, which provide for both thermal stability and resuscitation, are heavy, not suited for portability, and are complex and expensive.

Radiant warmers typically afford easy access to the patient without disturbing the thermal environment. The infant is normally located on a bed which may be surrounded by a peripheral barrier which serves to inhibit convective heat loss.

However, radiant warmers that are currently known and available are heavy and very bulky. Delivery of such warmers to remote areas requires the use of vehicles with a significant cargo capacity. A typical ambulance would not have room to accommodate such a unit without removing standard equipment such as the stretcher. Specialized lift mechanisms or multiple people capable of lifting and maneuvering the large warmer are also required. In rural environments, bringing such a device to a mother in labor may be impracticable. Further, such systems may be too expensive for communities with modest healthcare budgets.

An alternative to the typical prior art infant radiant warmer in terms of size, bulk, and weight would enable the ready use of radiant warming with infants delivered in rural and/or low resource settings. Such an alternative warmer would ideally be able to provide the same functionality as known warmers but would also be reconfigurable to make it more easily transported and deployed.

SUMMARY

In order to overcome the complexity and bulk of the prior art infant radiant warmers, the present disclosure provides for a reconfigurable, foldable, and manually transportable infant radiant warmer. The slim configuration when in a collapsed configuration enables the warmer to be conveyed within a vehicle such as an ambulance while not consuming a significant amount of space. Further, the collapsed warmer is provided with wheels and a handle that enable one person to easily relocate the unit to a remote location. The small size when collapsed requires a relatively small space for storage, a benefit for medical facilities of limited size and resources. At the same time, the presently disclosed reconfigurable warmer may also assume a deployed configuration in which open access to an infant lying on a bed platform is provided while the infant receives warmth from a radiant heater disposed upon an adjacent mast.

In addition to enabling temperature maintenance for a newborn patient, one embodiment of the presently disclosed device is also equipped for full resuscitation, thus significantly increasing the chances of survivability. The portability of such a unit thus enables the provision of critical thermal and cardiac and/or pulmonary resuscitation in remote settings, thereby reducing the mortality and morbidity of these fragile patients.

The reconfigurable infant radiant warmer of the present disclosure is comprised of at least three main components: a bed module; a mast module; and a suspension module. The bed module includes a bed platform for receiving an infant, a bassinet frame surrounding the bed platform, and a mattress on the bed platform. The bassinet frame is provided with a notch at one end of the bed module. Ideally, accommodation is provided for a battery which is used to power the electronics including the radiant heater. A solar panel may also be integrated into the disclosed system.

The mast module may include a mast, a radiant heater, which may be an IR ceramic heater, an observation lamp for illuminating the bed module, an accessory mounting pole substantially parallel to the mast, a utility tray for supporting diagnostic equipment such as a resuscitation unit, a user interface, an interface for a thermal sensor, and a locking hinge for attaching the mast to the bed module. The interface may take a variety of forms, including a digital display, a touchpad, and a keypad. Visual and aural annunciators may also be provided. The locking hinge enables the mast to be oriented substantially orthogonal to the bed module in a deployed configuration and substantially parallel to the bed module when in the collapsed configuration. The bassinet frame notch facilitates the positioning of the mast in the collapsed configuration.

The suspension module is disposed beneath the bed module and serves to both support the reconfigurable infant radiant warmer during use, in the deployed configuration, and to enable the easy transport of the warmer by a single user, in the collapsed configuration. In a first embodiment, the suspension module comprises legs, or frames, that rotatably intersect in an X-shape when in the deployed configuration and that are substantially parallel when in the collapsed configuration. A first of the frames is a base frame that is pivotably attached at one end to the underside of the bed platform. It may be rectangular in shape. A second of the frames is a mobility frame that is also pivotably attached at one end to the underside or side of the bed platform. The mobility frame may be U-shaped with free ends at a lower extent, with wheels disposed thereon. At an upper extent, the mobility frame preferably forms a handle. Intermediate the base frame and the mobility frame is a hinge that enables the frames to rotate relative to each other. The hinge may be locking to assist in maintaining the warmer in either the deployed or collapsed configuration. When the warmer is in the collapsed configuration, the wheels at the lower extent of the mobility frame extend beyond the bed platform and the handle at the upper extent of the mobility frame projects away from the bed platform.

In a second embodiment, the suspension module includes first and second utility frames joined at an upper extent thereof by a hinge. Each utility frame includes parallel legs having at least one wheel at a lower extent thereof, the wheels each having a horizontal axis of rotation. The suspension module also includes a primary stand connected to the first and second utility frames by the hinge. In a deployed configuration of the second warmer embodiment, the first and second utility frames and the primary stand form an invert Y-shape, with the wheels on the ground and the primary stand projecting upwards.

The upper extent of the primary frame is pivotably mounted to one end of the bed module. In the deployed configuration, the bed module extends horizontally with respect to the vertical primary stand. The mast module also extends vertically above the primary stand.

In the collapsed configuration of this second embodiment, the first and second utility frames are mutually adjacent, with the wheels of the second utility frame extending downward. Both utility frames are adjacent the underside of the bed module. The mast module is rotated down and into the bassinet frame of the bed module. A handle portion of the primary stand is extended upwards, forming a handle by which the collapsed warmer may be manually transported on the second utility frame wheels.

The reconfigurable infant warmer is solar powered in one embodiment. This is important for use in remote locations lacking in any or reliable line power. This may also contribute to a lower weight unit. Embodiments include accommodations for ancillary medical equipment including gas cylinders, such as oxygen tanks, resuscitation units, heart monitors, etc.

BRIEF DESCRIPTION OF THE DRAWINGS

Illustrative embodiments of the disclosed technology are described in detail below with reference to the attached drawing figures, which are incorporated by reference herein and wherein.

DETAILED DESCRIPTION

Figure 1:
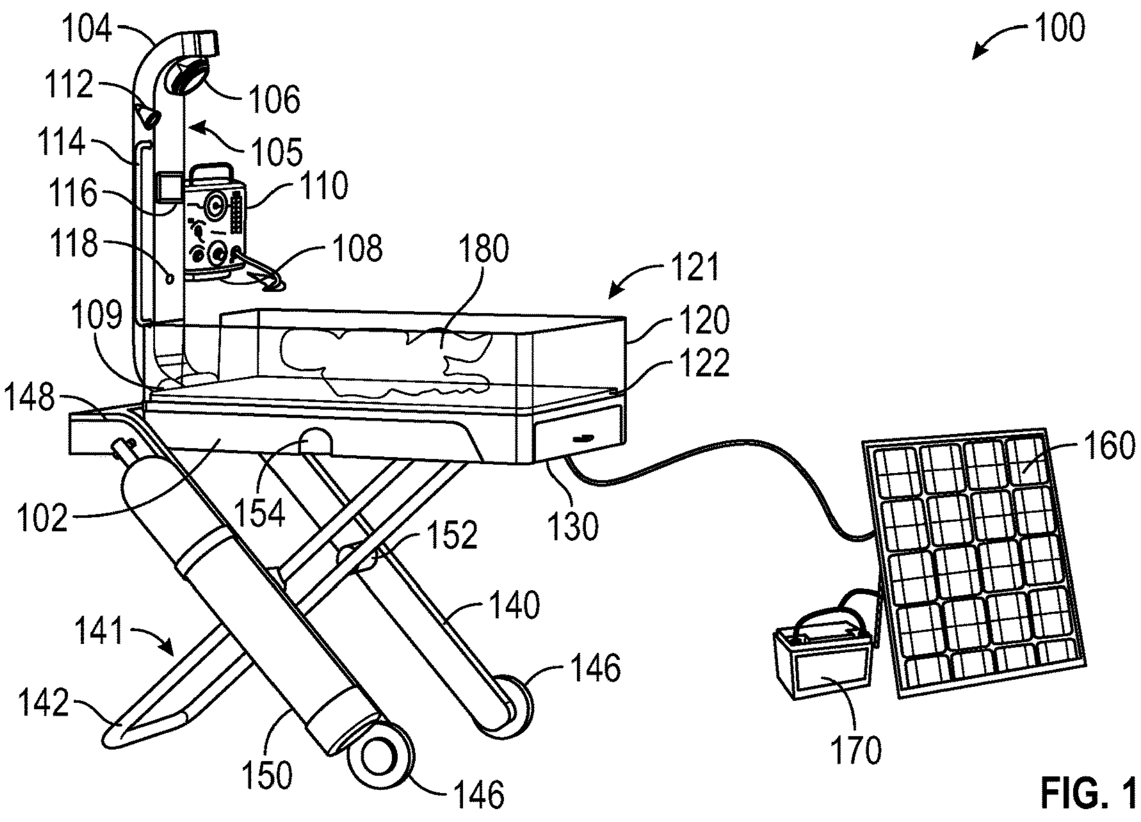
FIG. 1 is a perspective view of a portable, folding infant radiant warmer according to the present disclosure shown in a deployed configuration.

Disclosed herein is a reconfigurable, foldable, and manually transportable infant radiant warmer. A collapsed configuration minimizes the footprint required for storing the warmer and enables convenient manual transportation, while a deployed configuration provides a fully functional warmer.

Various aspects of at least one embodiment of the present invention are discussed below with reference to the accompanying figures. It will be appreciated that, for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, however, not every component may be labeled in every drawing. The figures are provided for the purposes of illustration and explanation and are not intended as a definition of the limits of the invention.

With respect to FIG. 1, a portable, folding infant warmer 100 is depicted in the deployed configuration. The warmer includes a substantially rectangular bed module 121, a mast module 105 disposed at one end of the bed module, and a suspension module 141 disposed beneath the bed module. Many of the elements of the embodiment of FIG. 1 are also seen in exploded form in FIG. 2.

The bed module 121 includes a bed platform 122 and an upright bassinet frame 120 which extends peripherally about the bed platform. The bed platform and bassinet frame together define a treatment area where an infant 180 may be placed. A mattress or other cushioning material may be disposed within the treatment area and, if provided, is fluid impervious and easily cleaned or disposable.

One end of the bassinet frame 120 may include a discontinuity or notch at a proximal end of the bed platform for receiving a mast 104 therein when the warmer 100 is in the collapsed configuration, as will be discussed subsequently. The bassinet frame is preferably formed of a transparent, pliant material such as acrylic. The bed platform may also comprise a storage drawer 130 which may open from a distal end of the bed platform. A notch 154 may be provided on either side of the bed platform for accommodating a rotating frame hinge 152 when the warmer is in the collapsed configuration, as will be discussed subsequently. The notch may be provided with a locking mechanism for engaging with the frame hinge and for restraining the frame hinge in the collapsed configuration.

Other optional elements of the bed module 121 include storage space for a battery 170 and/or an electrical transformer (not shown), such as for converting current from a solar panel 160 to line current required to operate electric instruments associated with the warmer, as will be discussed subsequently.

The mast module 105 illustrated in FIG. 1 includes a mast 104, a radiant heater 106 disposed towards an upper end of the mast, and a mast hinge 109 disposed at a lower end of the mast. The radiant heater may be a quartz or ceramic radiant heater. The mast hinge is rotatably connected to the proximal end of the bed platform 122, and enables the mast to selectively rotate about a horizontal axis from an upwardly extending position when the warmer 100 is in the deployed configuration to a substantially laterally extending position, extending through the bassinet frame 120 notch and lying proximate the bed platform 122, when in the collapsed configuration. The mast hinge is selectively lockable in one embodiment to maintain the mast in the desired position relative to the bed module 121.

The mast module 105 may further include, in certain embodiments, an observation lamp 112 oriented for illuminating the bed platform 122. An accessory mounting pole 114 may be disposed on and parallel to the mast 104 for enabling additional equipment to be mounted thereon. A utility tray 108 may also be disposed on the mast to provide a platform for equipment such as an optional resuscitation unit 110. Preferably, the accessory pole and utility tray are mounted on the mast such that they do not interfere with the orientation of the mast in the laterally extending position. Alternatively, the accessory pole and utility tray are removable.

Figure 2:
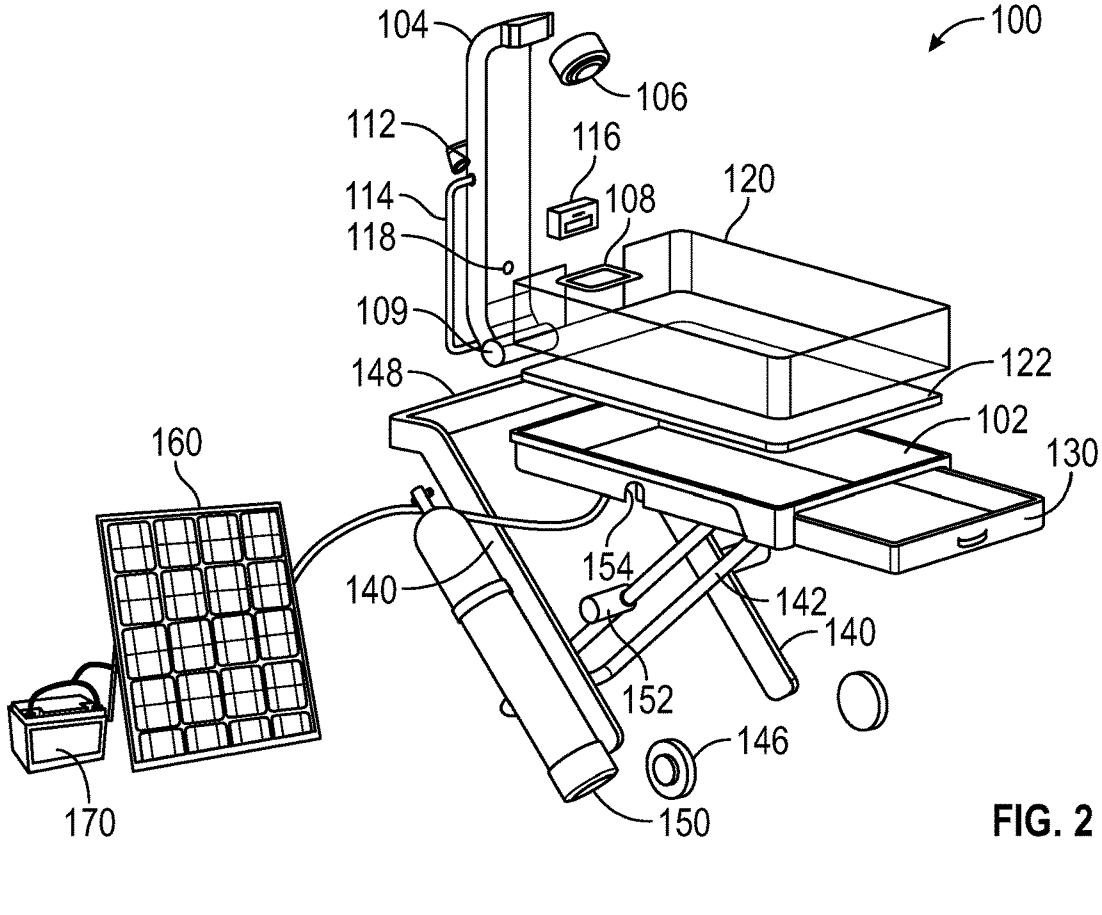
FIG. 2 is an exploded perspective view of the warmer of FIG. 1.

The warmer 100 illustrated in FIGS. 1 and 2 further includes a mast 104 having a user interface 116. The interface may be implemented in a variety of ways. For example, the user interface may include a display unit capable of displaying data such as heartbeat, temperature, time, etc. The user interface may also include a control panel capable of receiving user input, such as via a touch screen, keypad, dials, pushbuttons, etc.

The mast 104 may include in one embodiment a thermal sensor interface 118 for receiving a cable associated with a thermal sensor (not illustrated) to be placed on or in a body cavity of an infant disposed on the bed module 121. The output of such a sensor may be processed by a data processor (not shown) integrated into the mast module 105 or bed module. For example, the data processor may be a printed circuit board integrated into or in communication with the user interface 116, which may then provide a representation of the sensed temperature as an output to a user. The user may set a desired sensed body temperature via the user interface. The user interface may, in response to output from the data processor, provide a visual and/or aural annunciation of alarm conditions which are definable by the user. Such alarm conditions may include low and/or high body temperature. Wireless technologies such as Bluetooth may be integrated into the user interface and/or data processor to enable wireless interfacing with a user mobile device, such as a tablet computer or smart phone.

The suspension module 141 illustrated in FIGS. 1 and 2 includes a base frame 142 and a mobility frame 140 interconnected by a frame hinge 152. The base frame is rotatably connected to the underside of the bed module 121 such that, in the warmer 100 deployed configuration, the base frame extends at an acute angle to the bed platform 122 and, in the warmer collapsed configuration, the base frame is substantially parallel to the underside of the bed platform. The latter configuration, shown in FIG. 3, will be discussed subsequently. The base frame as illustrated is substantially rectangular with one narrow end connected to the bed platform and the opposite narrow end configured to rest on the ground when the warmer is in the deployed configuration, as shown in FIG. 1. In another embodiment, the base frame is not a complete rectangle, with either the upper narrow end being discontinuous and configured for rotation with respect to the bed platform or the lower narrow end forming feet (not shown) for engaging the ground.

The mobility frame 140 as illustrated is substantially U-shaped. The upper end of the mobility frame includes a handle portion 148, formed by the upper, closed end of the mobility frame, that may extend out of the plane of the remainder of the mobility frame. When the warmer 100 is in the deployed configuration, as shown in FIG. 1, the handle portion extends away from the bed module 121.

The opposite narrow end of the mobility frame 140 includes two long arms that each terminate in a respective free end. Disposed on each free end is a respective wheel 146. While each free end in FIGS. 1 and 2 has one wheel, other non-illustrated embodiments may have plural wheels. Each wheel has a common horizontal axis of rotation in the illustrated embodiment. In the deployed configuration, the base frame 140 end on the ground prevents the warmer 100 from rolling on the wheels. In another embodiment, the wheels are replaced with skids.

Figure 3:
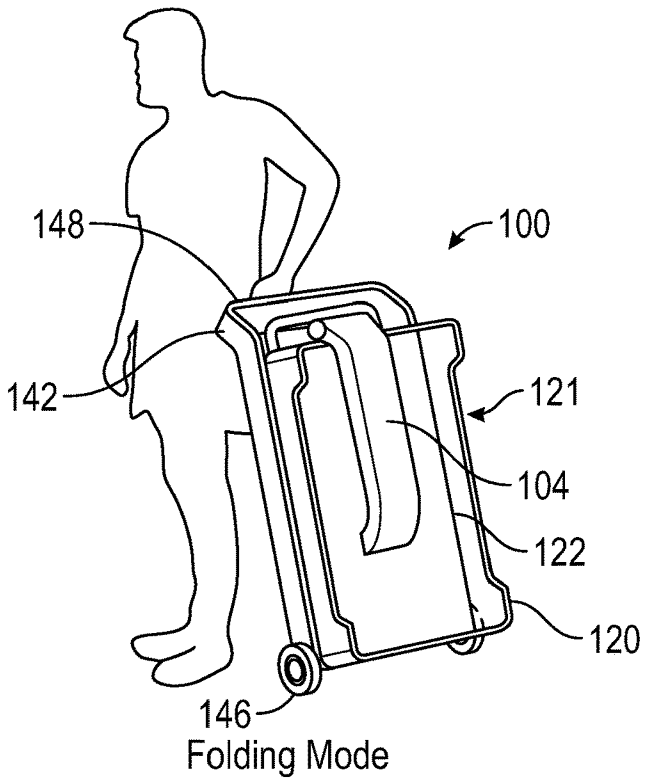
FIG. 3 is a perspective view of the warmer of FIG. 1 shown in a collapsed configuration.

The frame hinge 152 may be provided with a locking mechanism such that the base frame 142 and mobility frame 140 may be maintained in either the deployed configuration (FIGS. 1 and 2) or the collapsed configuration (FIG. 3). Alternatively, the mobility frame and/or the bed platform 122 may have mechanical features enabling selective engagement for retaining the two portions in either configuration. When the warmer 100 is in the collapsed configuration, the frame hinge 152 is configured to fit within the notch 154 within the lower edge of the bed platform 122.

When the warmer 100 is in the collapsed configuration, as seen in FIG. 3, the mobility frame 140 is substantially parallel to the bed module 121 and at least a distal portion of the wheels 146 extends beyond the distal end of the bed module so that the warmer may roll on the wheels without the remainder of the assembly touching the ground. Also in this configuration, the handle 148 extends up and away from the remainder of the warmer when manually elevated into a transport position, as seen in FIG. 3.

The suspension module 141 in general, and the mobility frame 140 in particular, may also include an oxygen cylinder receptacle 150 for selectively receiving an oxygen cylinder therein.

As noted above, certain embodiments of the warmer 100 as presently disclosed may include a solar panel 160, such as a 12 volt solar panel, which may be connectable via one or more conductors to electronics within the warmer, such as a transformer (not shown) or battery 170, such as a 12 volt, 50 amp hour lithium ion deep cycle battery. In particular, the rear face of the solar panel may be provided with mechanical features enabling it to be fastened to complimentary mechanical features provided on an upper edge of the bassinet frame 120. With such features, the solar panel may be attached to the top of the bassinet frame once the warmer 100 is in the collapsed configuration with the mast module 105 stowed within the bed module 121. This serves the purpose of enabling easy transport of the solar panel along with the collapsed warmer as well as reducing the quantity of foreign objects, dirt, and dust entering the bed module during transport or storage.

Figure 4:
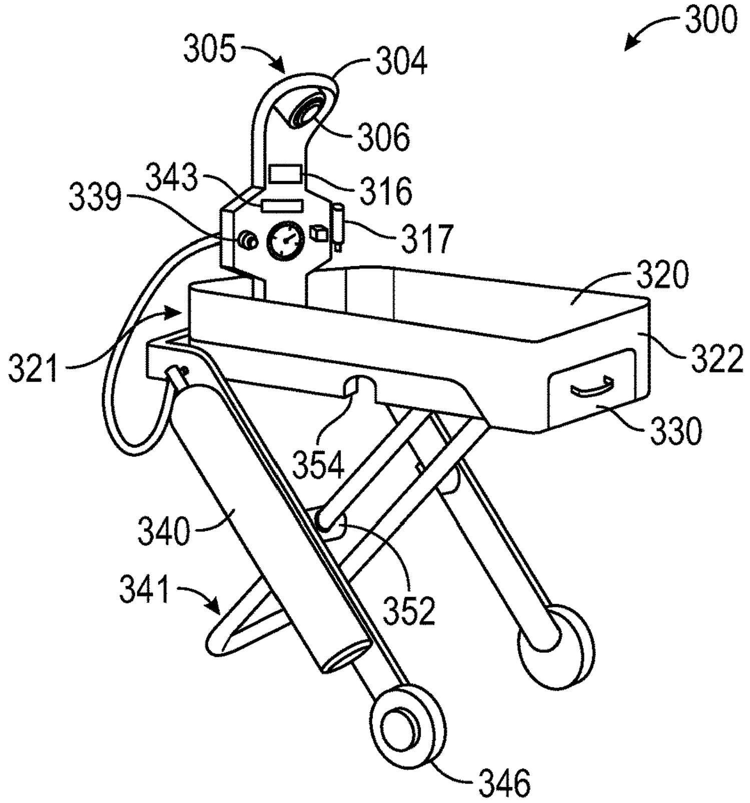
FIG. 4 is a perspective view of a second embodiment of a portable, folding infant radiant warmer according to the present disclosure shown in a deployed configuration.

Another embodiment of the presently disclosed reconfigurable, foldable, and manually transportable infant radiant warmer 300 is illustrated in FIG. 4. This embodiment shares many of the same features as shown and described with respect to FIGS. 1-3. For example, the embodiment of FIG. 4 includes a mast module 305, a bed module 321, and a suspension module 341.

The bed module 321 includes a bed platform 322 and an upright bassinet frame 320 which extends peripherally about the bed platform. The bed platform and bassinet frame together define a treatment area for receiving an infant. A mattress or other cushioning material, forming a bed, may be disposed within the treatment area and, if provided, is fluid impervious and easily cleaned or disposable.

One end of the bassinet frame 320 may include a discontinuity or notch at a proximal end of the bed platform 322 for receiving a mast 304 therein when the warmer 300 is in the collapsed configuration. The bassinet frame is preferably formed of a transparent, pliant material such as acrylic. The bed platform may also comprise a storage drawer 330 which may open from a distal end of the bed platform. The storage drawer may provide storage for a resuscitation kit, among other resources. A notch 354 may be provided on either side of the bed platform for accommodating a rotating frame hinge 352 when the warmer is in the collapsed configuration. The notch may be provided with a locking mechanism for engaging with the frame hinge and for restraining the frame hinge in the collapsed configuration.

The mast module 305 illustrated in FIG. 4 includes a mast 304, a radiant heater 306 disposed towards an upper end of the mast, and a mast hinge (not shown) disposed at a lower end of the mast. The radiant heater may be a quartz or ceramic radiant heater. The mast hinge is rotatably connected to the proximal end of the bed platform 322, and enables the mast to selectively rotate about a horizontal axis from an upwardly extending position when the warmer 300 is in the deployed configuration to a substantially laterally extending position, extending through the bassinet frame 320 notch and lying proximate the bed platform 322, when in the collapsed configuration. The mast hinge is selectively lockable in one embodiment to maintain the mast in the desired position relative to the bed module 321.

The mast module 305 may further include, in certain embodiments, a suctioning outlet 317 connectable to a source of vacuum and an oxygen outlet 339 connectable to a source of oxygen gas, such as from an associated oxygen cylinder 340. A timer 343 may also be provided on the mast for use in determining an APGAR score.

The warmer 300 illustrated in FIG. 4 further includes a mast 304 having a user interface 316. The interface may be implemented in a variety of ways. For example, the user interface may include a display unit capable of displaying data such as heartbeat, temperature, time, etc. The user interface may also include a control panel capable of receiving user input, such as via a touch screen, keypad, dials, pushbuttons, etc.

The suspension module 341 illustrated in FIG. 4 is essentially the same as described above with respect to FIGS. 1 and 2, including a base frame and a mobility frame, having wheels 346, interconnected by a frame hinge 352. When the warmer 300 is in a collapsed configuration, the frame hinge 352 is configured to fit within the notch 354 within the lower edge of the bed platform 322.

The collapsed configuration of the embodiment of FIG. 4 is essentially comparable to the collapsed configuration of the embodiment of FIGS. 1 and 2, as illustrated in FIG. 3.

Figure 5:
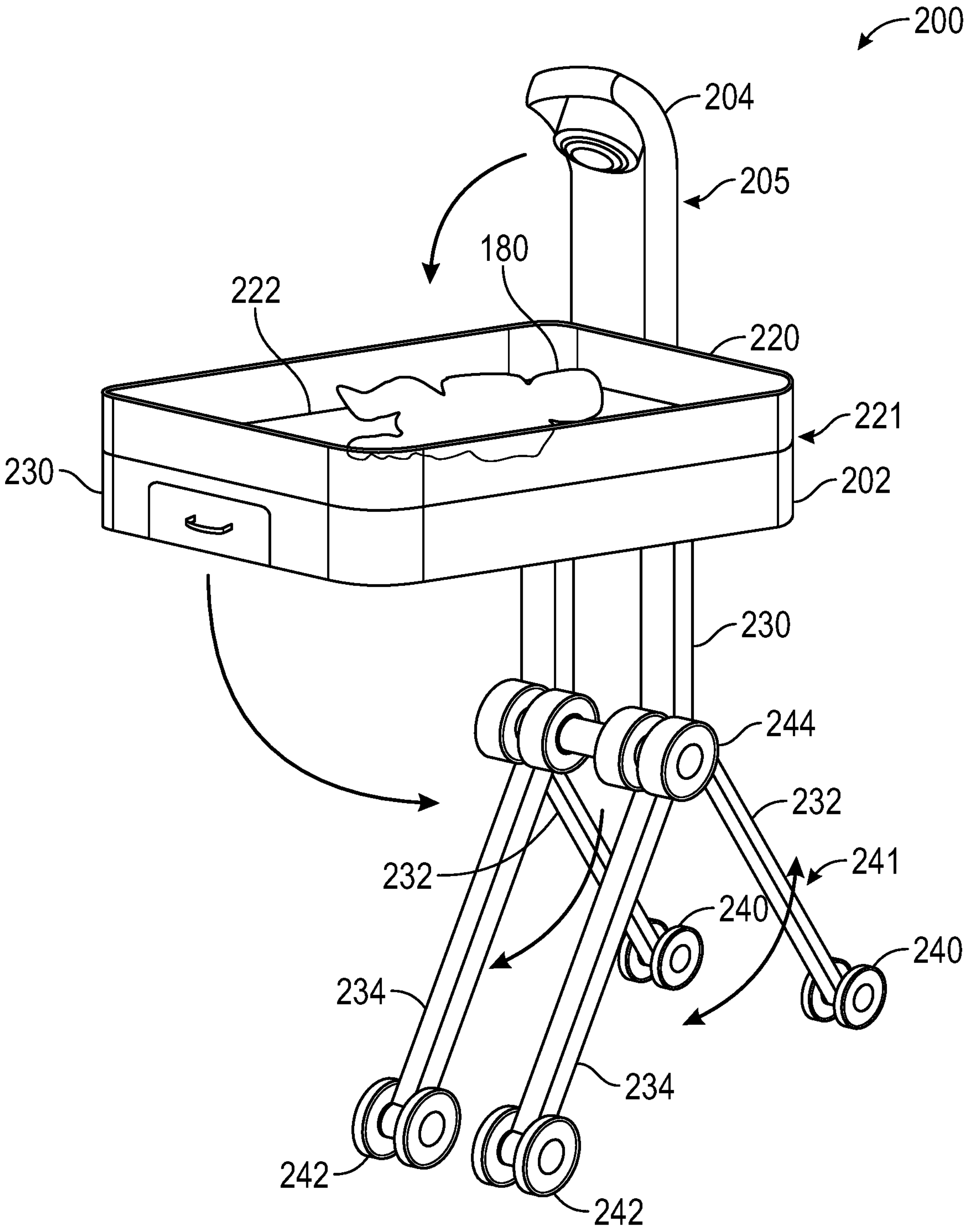
FIG. 5 is a perspective view of a third embodiment of a portable, folding infant radiant warmer according to the present disclosure shown in a deployed configuration.
Figure 6:
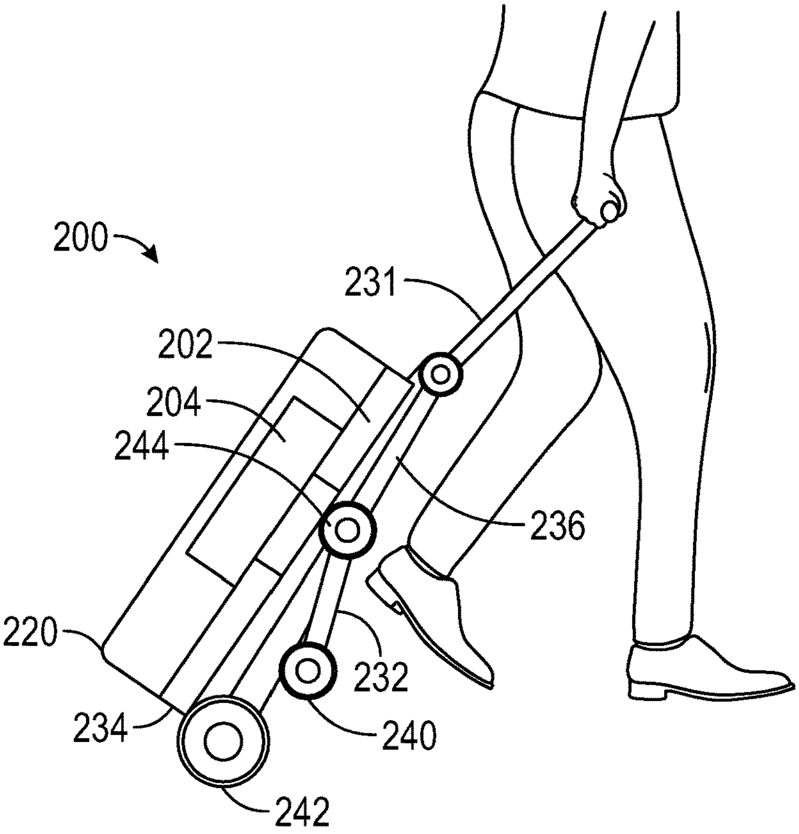
FIG. 6 is a side elevation view of the second embodiment of FIG. 5 shown in a collapsed configuration.
Figure 7:
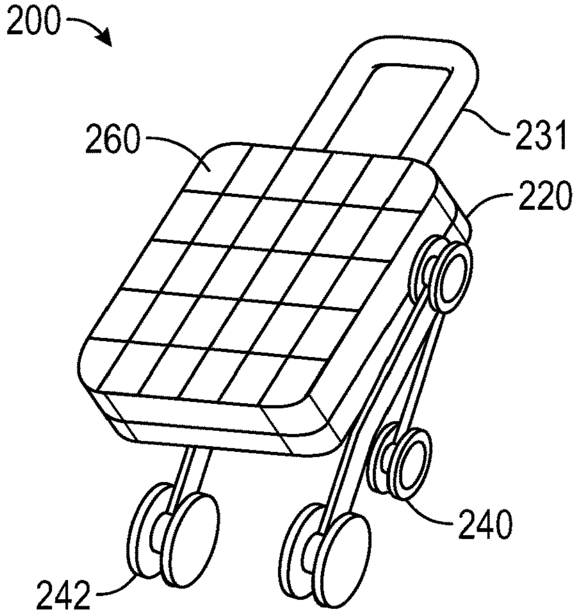
FIG. 7 is a perspective view of the second embodiment of FIG. 5 shown in a collapsed configuration with an attached solar panel.

Another embodiment of the presently disclosed reconfigurable, foldable, and manually transportable infant radiant warmer 200 is illustrated in FIGS. 5-7. In particular, with regard to FIG. 5, this embodiment comprises a bed module 221, a mast module 205, and a suspension module 241. The former two elements are substantially similar to those described above with respect to FIGS. 1-3.

Thus, the mast module 205 includes a mast 204 which may have other ancillary components attached thereto, such as a radiant heater, observation lamp, accessory mounting pole, utility tray, user interface, and thermal sensor interface, as shown and described with respect to FIGS. 1 and 2. The bed module 209 likewise includes a bed platform 202, bassinet frame 220, mattress or cushioning material comprising a bed 222 for receiving an infant 180, and a storage drawer 230.

The suspension module 241 of the embodiment of FIGS. 5-7 differs from that of the embodiment of FIGS. 1-3. Specifically, the suspension module in FIG. 5 includes a first utility frame 232, a second utility frame 234, and a primary stand 236. Each of the first utility frame, the second utility frame, and the primary stand are rotatably interconnected by a frame hinge 244, which may include the capability of being selectively locked in either a deployed or collapsed configuration, as will be described in further detail below.

As illustrated, each of the first utility frame 232 and the second utility frame 234 comprises a pair of mutually parallel legs, an upper end of which is rotatably attached to the frame hinge 244 and a lower end of which has rotatably attached thereto at least one wheel 240, 242, respectively. As shown in FIGS. 5 and 7, each leg is provided with two parallel wheels.

The primary stand 236 extends between the frame hinge 244 and the bed module 221. The primary stand is rotatably connected to a proximal end of the bed platform 202. In a deployed configuration, such as shown in FIG. 5, the bed module extends horizontally with respect to the primary stand, such as through a locking hinge (not shown). This locking hinge maintains the bed module in the horizontal orientation while in the deployed configuration, and allows the primary stand and the underside of the bed platform to be mutually adjacent in a collapse configuration.

The mast 204 in the embodiment of FIG. 5 is also configured to be selectively rotatable about a horizontal axis of rotation whereby the mast extends substantially vertically in the deployed configuration and is received within the bassinet frame 220 through a notch therein (not shown in FIG. 5) in a collapsed configuration. The mast hinge is thus selectively lockable. The mast hinge is, in one embodiment, the same as or coincident with the lock hinge that interconnects the suspension module 241 and the bed module 221.

In the warmer 200 collapsed configuration, seen in FIGS. 6 and 7, the first utility frame 232, with respective wheels 240, is brought adjacent the second utility frame 234 and respective wheels 242 about the frame hinge 244. The frame hinge is then locked in place to maintain this relative orientation of utility frames. As best seen in FIG. 6, the wheels 242 of the second utility frame 234 extend downwardly, farther than the wheels 240 of the first utility frame 232. This enables the warmer 200 to be manually conveyed in the collapsed configuration on the wheels of the second utility frame.

The primary stand 236 also includes a retractable handle portion 231. The handle portion may be attached to the remainder of the primary stand via a handle hinge (not shown), which in one embodiment is the same hinge or coincident with the hinge interconnecting the mast 204 with the bed module 221 and/or the lock hinge interconnecting the suspension module 241 with the bed module. In this embodiment, the handle portion may be selectively swung up and away from the frame hinge 244 to form a handle extending above the warmer 200, as seen in FIGS. 6 and 7.

In another embodiment, the handle portion may be attached to the remainder of the primary stand via a friction receptacle, whereby the handle portion may be laterally slid along the length of the primary stand 236, thereby forming the handle visible in FIGS. 6 and 7.

The embodiment of FIGS. 5-7 may also include an optional solar panel 260. As described above, the solar panel may include mechanical features on its underside to enable the solar panel to be selectively received by complimentary mechanical features formed on an upper edge of the bassinet frame 220, as seen in FIG. 7.

The foregoing description has been directed to particular embodiments. However, other variations and modifications may be made to the described embodiments, with the attainment of some or all of their advantages. It will be further appreciated by those of ordinary skill in the art that modifications to the above-described systems and methods may be made without departing from the concepts disclosed herein. Accordingly, the invention should not be viewed as limited by the disclosed embodiments. Furthermore, various features of the described embodiments may be used without the corresponding use of other features. Thus, this description should be read as merely illustrative of various principles, and not in limitation of the invention.

Many changes in the details, materials, and arrangement of parts and steps, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

We claim:

1. A portable, folding radiant infant warmer, comprising:
- a substantially rectangular bed module comprising
  - a bed platform, and
  - a bassinet frame;
- a mast module disposed at one end of the bed module and comprising
  - a mast,
  - a radiant heater disposed on the mast, and
  - a mast hinge in communication with a lower end of the mast and a proximal end of the bed module for enabling the mast to be selectively rotated relative to the bed module; and
  - a suspension module disposed beneath the bed module and comprising
  - a reconfigurable base, and
  - a pair of wheels disposed on the reconfigurable base, wherein the mast hinge further comprises a locking mechanism for releasably fixing the mast at one of a deployed position wherein the mast is substantially orthogonal to a plane defined by the bed platform and a collapsed position wherein the mast is at least partially disposed within the bassinet frame.

2. The warmer of claim 1, wherein the bed module comprises a storage drawer within the bed platform at an end of the bed module opposite the mast module.

3. The warmer of claim 1, wherein the bed module comprises a battery storage compartment for selectively receiving a battery therein.

4. The warmer of claim 1, wherein the bed module comprises a transformer storage compartment for selectively receiving a transformer therein.

5. The warmer of claim 1, wherein the bassinet frame is comprised of clear acrylic.

6. The warmer of claim 1, wherein the bassinet frame comprises a notch proximate the mast hinge for enabling the mast to be at least partially received within the bassinet frame.

7. The warmer of claim 1, further comprising a mattress dimensioned to be disposed within the bassinet frame.

8. The warmer of claim 1, wherein the radiant heater is an infrared ceramic heater.

9. The warmer of claim 1, wherein the mast module further comprises an observation lamp.

10. The warmer of claim 1, wherein the mast module further comprises an accessory mounting pole.

11. The warmer of claim 10, wherein the accessory mounting pole is substantially parallel to the mast.

12. The warmer of claim 1, wherein the mast module further comprises a utility tray in mechanical communication with the mast.

13. The warmer of claim 12, wherein the mast module further comprises a resuscitation module disposed upon the utility tray.

14. The warmer of claim 1, wherein the mast module further comprises a user interface disposed in conjunction with the mast.

15. The warmer of claim 14, wherein the user interface comprises a display unit.

16. The warmer of claim 14 wherein the user interface comprises a control panel.

17. The warmer of claim 14, wherein the user interface comprises a printed circuit board.

18. The warmer of claim 1, wherein the mast module further comprises a thermal sensor interface.

19. The warmer of claim 1, wherein the suspension module comprises:
- a frame hinge;
- a base frame having a proximal end in communication with an underside of the bed module and a distal end; and
- a mobility frame having a proximal end and a distal end,
- wherein the frame hinge intersects each of the base frame and the mobility frame at a midpoint thereof, thereby rotatably coupling the base frame and the mobility frame.

20. The warmer of claim 19, wherein, when the proximal end of the mobility frame is in selective communication with the underside of the bed module at a proximal end thereof, the distal ends of the base frame and mobility frame are separated.

21. The warmer of claim 19, wherein, when a majority of the length of the mobility frame is proximate the underside of the bed module, a majority of the length of the base frame is also proximate the underside of the bed module.

22. The warmer of claim 21, further comprising plural wheels disposed on the distal end of the mobility frame.

23. The warmer of claim 22, wherein, when the majority of the length of the mobility frame is proximate the underside of the bed module, the plural wheels extend beyond a distal end of the bed module.

24. The warmer of claim 19, wherein the proximal end of the mobility frame comprises a handle.

25. The warmer of claim 19, wherein the mobility frame comprises a gas tank receptacle for selectively receiving a gas tank therein.

26. The warmer of claim 1, further comprising at least one solar panel in selective electrical communication with the radiant heater.

27. The warmer of claim 26, wherein a first of the at least one solar panel comprises mechanical features for releasably fixing the first solar panel on an upper edge of the bassinet frame.

28. The warmer of claim 1, further comprising at least one battery in communication with the radiant heater.

29. A portable, folding radiant infant warmer, comprising:

a substantially rectangular bed module comprising
  a bed platform, and
  a bassinet frame;
a mast module disposed at one end of the bed module and comprising
  a mast
  a radiant heater disposed on the mast, and
  a mast hinge in communication with a lower end of the mast and a proximal end of the bed module for enabling the mast to be selectively rotated relative to the bed module; and
a suspension module disposed beneath the bed module and comprising
  a reconfigurable base, and
  a pair of wheels disposed on the reconfigurable base;

wherein the suspension module comprises:

a frame hinge;
a primary stand having a proximal end and a distal end, the proximal end in rotatable communication with one end of the bed module and the distal end in communication with the frame hinge;
a first wheel frame having a proximal end, a distal end, and plural first frame wheels, the proximal end in communication with the frame hinge and the distal end in communication with the first frame plural wheels, and
a second wheel frame having a proximal end, a distal end, and plural second frame wheels, the proximal end in communication with the frame hinge and the distal end in communication with the plural second frame wheels.

30. The warmer of claim 29, wherein the frame hinge comprises a hinge lock for selectively maintaining the frame hinge in at least first and second positions, wherein the first frame and the second frame are separated in the first position, and wherein the first frame and the second frame are mutually adjacent in the second position.

31. The warmer of claim 29, further comprising a primary stand hinge intermediate the primary stand and the bed module for enabling rotatable communication therebetween.

32. The warmer of claim 29, wherein the primary stand further comprises an extendible handle.

33. A portable, folding radiant infant warmer, comprising:

a substantially rectangular bed module comprising
  a bed platform, and
  a bassinet frame;
a mast module disposed at one end of the bed module and comprising
  a mast
  a radiant heater disposed on the mast;
  a mast hinge in communication with a lower end of the mast and a proximal end of the bed module for enabling the mast to be selectively rotated relative to the bed module; and
a suspension module disposed beneath the bed module and comprising
  a reconfigurable base, and
  a pair of wheels disposed on the reconfigurable base;

further comprising at least one solar panel in selective electrical communication with the radiant heater and a transformer intermediate the at least one solar panel and the radiant heater.

* * * * *